United States Patent

Paust et al.

Patent Number: 5,294,731
Date of Patent: Mar. 15, 1994

[54] PREPARATION OF β-HYDROXYCARBOXYLATES

[75] Inventors: Joachim Paust, Neuhofen; Wolfgang Siegel, Mannheim, both of Fed. Rep. of Germany

[73] Assignee: BASF Aktiengesellschaft, Ludwigshafen, Fed. Rep. of Germany

[21] Appl. No.: 36,023

[22] Filed: Mar. 23, 1993

[30] Foreign Application Priority Data

Mar. 25, 1992 [DE] Fed. Rep. of Germany ....... 4209616

[51] Int. Cl.$^5$ .................. C07C 69/76; C07C 69/66
[52] U.S. Cl. .................. 560/60; 560/139; 560/126; 560/186; 554/150; 554/213
[58] Field of Search .......... 560/60, 126, 179, 186; 554/150, 213

[56] References Cited

PUBLICATIONS

CA 102(5):46055z 1984.
Bull. Chem. Soc., 53, 3301 (1980).
Tetrahedron Lett. 88 6481 (1987).
Synth. Comm 17, 1 (1987).
Synthesis 452 (1975).
Organometallics 5, 1257 (1986).
J. Org. Chem. 47, 5030 (1982).

Primary Examiner—Paul J. Killos
Attorney, Agent, or Firm—Keil & Weinkauf

[57] ABSTRACT

A process for the preparation of β-hydroxycarboxylates of the general formula I

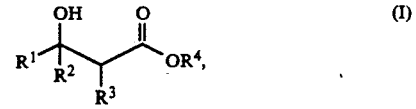

in which
$R^1$ and $R^2$ individually denote
$C_1$–$C_{20}$ alkyl optionally substituted by $C_1$–$C_8$ alkoxy and/or halogen, $C_3$–$C_{20}$ alkoxycarbonylalkyl, $C_2$–$C_{20}$ alkenyl, $C_5$–$C_{30}$ acetalalkenyl, aryl optionally mono- to penta-substituted by $C_1$–$C_8$ alkyl, $C_1$–$C_8$ alkoxy, and/or halogen, $C_7$–$C_{20}$ aralkyl, $C_7$–$C_{20}$ aralkenyl, hetaryl, $C_3$–$C_{20}$ cycloalkyl, or $C_4$–$C_{20}$ cycloalkylalkyl,
or together denote a $C_2$–$C_8$ alkylene chain
and one or other of $R^1$ and $R^2$ denotes hydrogen, and
$R^3$ denotes hydrogen, $C_1$–$C_{20}$ alkyl, $C_2$–$C_{20}$ alkenyl, aryl optionally mono- to penta-substituted by $C_1$–$C_8$ alkyl, $C_1$–$C_8$ alkoxy, and/or halogen, $C_7$–$C_{20}$ aralkyl, $C_3$–$C_{20}$ cycloalkyl, or $C_4$–$C_{20}$ cycloalkylalkyl, and
$R^4$ denotes $C_1$–$C_{20}$ alkyl, $C_4$–$C_{20}$ alkenyl, $C_7$–$C_{20}$ aralkyl, $C_3$–$C_{20}$ cycloalkyl, or $C_4$–$C_{20}$ cycloalkylalkyl,
by the reaction of carbonyl compounds of the general formula II

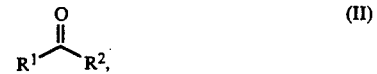

in which $R^1$ and $R^2$ have the meanings stated above, with α-bromocarboxylates of the general formula III

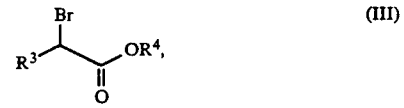

in which $R^3$ and $R^4$ have the meanings stated above, wherein the reaction with zinc is carried out in methylene chloride at a temperature ranging from 0° to 50° C.

1 Claim, No Drawings

PREPARATION OF β-HYDROXYCARBOXYLATES

This invention relates to a process for the preparation of β-hydroxycarboxylates by the reaction of carbonyl compounds with α-bromocarboxylates and zinc in methylene chloride at a temperature ranging from 0° to 50° C. and to the use of methylene chloride for effecting stable storage of α-bromozinc carboxylates.

α-Bromozinc carboxylates (Reformatskii compounds) can be reacted with a number of electrophilics, e.g., aldehydes, ketones, azomethines, nitriles, carboxylic chlorides, carboxylic anhydrides, carboxylates, lactones, and epoxides and are therefore significant for the preparation of important building blocks for organic syntheses and the production of naturally occurring substances.

To achieve good yields in the synthesis of β-hydroxycarboxylates by the reaction of carbonyl compounds with α-bromocarboxylates and zinc (Reformatskii-reaction) it is necessary to activate the zinc used or the entire reaction mixture by means of expensive methods.

Solvents primarily used are ethers such as diethyl ether, tetrahydrofuran, dioxane, ethylene glykol dimethyl ether, as well as dimethylformamide, dimethyl sulfoxide, acetonitrile, hexamethylphosphoric triamide, trimethyl borate, aromatic hydrocarbons such as benzene, and mixtures thereof.

The choice of solvent has a decisive influence on the safety of operation of the process, since the formation of the α-bromozinc carboxylates (Reformatskii-compounds) is accompanied by a strongly exothermic action, and when unduly high-boiling solvents are used a controllable reaction profile cannot be absolutely guaranteed for reaction mixtures in the quantities as are used on an industrial scale.

The use of alloys of zinc/silver is known from *Bull. Chem. Soc.* 53, 3301 (1980), *Tetrahedron Lett.* 88, 6481 (1987), *Synth. Comm.* 17, 1 (1987) for the preparation of α-bromozinc carboxylates and in the Reformatskii-reaction, respectively. The use of zinc prepared in situ in the reduction of zinc halides with alkali metals is recommended in *Synthesis* 452 (1975), and *Organometallics* 5, 1257 (1986) and *J. Org. Chem.* 47, 5030 (1982) suggests the use of ultrasonics for activation.

These methods of improving the yield of Reformatskii reactions are expensive and unusable on an industrial scale due to their considerable complexity.

It is thus an object of the present invention to overcome the aforementioned disadvantages.

Accordingly, we have found a novel and improved process for the preparation of β-hydroxycarboxylates of the general formula I,

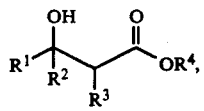

in which
$R^1$ and $R^2$ individually denote
$C_1$–$C_{20}$ alkyl optionally substituted by $C_1$–$C_8$ alkoxy and/or halogen, $C_3$–$C_{20}$ alkoxycarbonylalkyl, $C_2$–$C_{20}$ alkenyl, $C_5$–$C_{30}$ acetalalkenyl, aryl optionally mono- to penta-substituted by $C_1$–$C_8$ alkyl, $C_1$–$C_8$ alkoxy, and/or halogen, $C_7$–$C_{20}$ aralkyl, $C_7$–$C_{20}$ aralkenyl, hetaryl, $C_3$–$C_{20}$ cycloalkyl, or $C_4$–$C_{20}$ cycloalkylalkyl,
or together denote a $C_2$–$C_8$ alkylene chain
and one or other of $R^1$ and $R^2$ denotes hydrogen, and
$R^3$ denotes hydrogen, $C_1$–$C_{20}$ alkyl, $C_2$–$C_{20}$ alkenyl, aryl optionally mono- to penta-substituted by $C_1$–$C_8$ alkyl, $C_1$–$C_8$ alkoxy, and/or halogen, $C_7$–$C_{20}$ aralkyl, $C_3$–$C_{20}$ cycloalkyl, or $C_4$–$C_{20}$ cycloalkylalkyl, and
$R^4$ denotes $C_1$–$C_{20}$ alkyl, $C_4$–$C_{20}$ alkenyl, $C_7$–$C_{20}$ aralkyl, $C_3$–$C_{20}$ cycloalkyl or $C_4$–$C_{20}$ cycloalkylalkyl,
by the reaction of carbonyl compounds of the general formula II

in which $R^1$ and $R^2$ have the meanings stated above, with α-bromocarboxylates of the general formula III

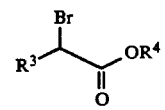

in which $R^3$ and $R^4$ have the meanings stated above, wherein the reaction with zinc is carried out in methylene chloride at a temperature ranging from 0° to 50° C., and a process for the preparation of α-bromozinc carboxylates of the general formula IV

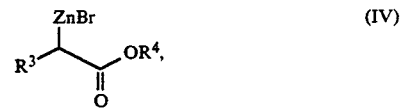

in which
$R^3$ denotes hydrogen, $C_1$–$C_{20}$ alkyl, $C_2$–$C_{20}$ alkenyl, aryl optionally mono- to penta-substituted by $C_1$–$C_8$ alkyl, $C_1$–$C_8$ alkoxy, and/or halogen, $C_7$–$C_{20}$ aralkyl, $C_3$–$C_{20}$ cycloalkyl, or $C_4$–$C_{20}$ cycloalkylalkyl, and
$R^4$ denotes $C_1$–$C_{20}$ alkyl, $C_4$–$C_{20}$ alkenyl, $C_7$–$C_{20}$ aralkyl, $C_3$–$C_{20}$ cycloalkyl, or $C_4$–$C_{20}$ cycloalkylalkyl,
from α-bromocarboxylates of the general formula III as defined above, wherein the reaction with zinc is carried out in methylene chloride at a temperature ranging from 0° to 50° C., and the use of methylene chloride for the stable storage of said α-bromozinc carboxylates IV.

The process of the invention may be carried out as follows:

The zinc can be placed in methylene chloride and the α-bromocarboxylate added at a controlled temperature, to form a solution of α-bromozinc carboxylate IV which is stable in storage. Such solutions can be reacted in situ with a carbonyl compound II by the addition thereof to a β-hydroxycarboxylate I, also at a controlled temperature.

Alternatively, the zinc may be placed in methylene chloride and a mixture of an α-bromocarboxylate IV and a carbonyl compound II may be added at a controlled temperature.

Another alternative is to place the zinc and the carbonyl compound in a vessel and to add the α-bromocarboxylate IV at a controlled temperature.

The thermal control can be effected by cooling the reaction mixture. The upper temperature limit is determined inter alia by the solvent methylene chloride (bp 42° C.) and is from ca 40° to 45° C. The reaction is carried out, as a general rule, at a temperature ranging from 0° to 50° C. and preferably at from 20° to 50° C. and more preferably at from 35° to 45° C.

The pressure under which the reaction is carried out is not crucial and can be set within wide limits. As a general rule, the process is carried out under a pressure which can range from 0.01 to 50 bar and preferably from 0.5 to 5 bar and is more preferably 1 bar (atmospheric pressure).

The solvent used is methylene chloride, which should be used preferably substantially in the absence of other solvents.

The zinc can be used in the form of tapes, balls, chips, or powder, and it is preferred to use the powder form. Zinc is used preferably substantially in the absence of other metals, such as more noble metals, e.g., copper and silver, i.e., it is preferred to use commercial zinc.

The β-hydroxycarboxylates I may be obtained by conventional methods such as extraction, distillation, chromatography, and crystallisation.

The present invention is a universal process for the preparation of Reformatskii compounds from commercial zinc and α-bromocarbonyl compounds and for the reaction thereof with electrophilics in methylene chloride as solvent.

Of particular advantage for industrial applications is the simplicity with which the Reformatskii synthesis can be carried out in methylene chloride, since neither the reactants nor the solvent have to be dried specially.

The activation of the zinc using, e.g., a catalytic amount of iodine is normally inadequate on its own but suffices in the present case to obtain excellent yields and high purity of the product in the reaction with electrophilics, whilst achieving very good space-time yields. The heat of reaction liberated during formation of the Reformatskii compound can be dissipated in a reliable manner, e.g., by means of cooling caused by evaporation of the methylene chloride and ensures that the reaction takes place safely without the need for intricate measuring and regulating means.

The substituents $R^1$, $R^2$, $R^3$, and $R^4$ in the formulas I, II, III, and IV have the following meanings:

$R^1$, $R^2$, $R^3$, and $R^4$

- $C_1$-$C_{20}$ alkyl and preferably $C_1$-$C_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably $C_1$-$C_4$ alkyl such as methyl, ethyl, n-propyl, isopropyl, n-butyl, isobutyl, sec-butyl, and tert-butyl,
- $C_2$-$C_{20}$ alkenyl and preferably $C_2$-$C_8$ alkenyl such as vinyl, allyl, but-2-en-1-yl, but-4-en-1-yl, but-4-en-2-yl, pent-2-en-1-yl, and 2,2-dimethyl-pent-1-en-1-yl,
- $C_7$-$C_{20}$ aralkyl and preferably $C_7$-$C_{12}$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl, and 4-phenylbutyl and more preferably benzyl, 1-phenethyl, and 2-phenethyl,
- $C_3$-$C_{20}$ cycloalkyl and preferably $C_3$-$C_8$ cycloalkyl such as cyclopropyl, cyclobutyl, cyclopentyl, cyclohexyl, cycloheptyl, and cyclooctyl and more preferably cyclopentyl, cyclohexyl, and cyclooctyl,
- $C_4$-$C_{20}$ cycloalkylalkyl and preferably $C_4$-$C_{12}$ cycloalkylalkyl such as cyclopentylmethyl and cyclohexylmethyl,
- $C_1$-$C_{20}$ alkyl substituted by $C_1$-$C_8$ alkoxy and/or halogen such as 2-methoxyethyl, 3-methoxypropyl, 3-methoxybutyl, 4-methoxybutyl, chloromethyl, 2-chloroethyl, and 3-chloropropyl, $R^1$, $R^2$, and $R^3$

- aryl, such as phenyl, 1-naphthyl, 2-naphthyl, 1-anthryl, 2-anthryl, and 9-anthryl and preferably phenyl, 1-naphthyl, and 2-naphthyl and more preferably phenyl,
- aryl mono- to penta-substituted by $C_1$-$C_8$ alkyl, $C_1$-$C_8$ alkoxy, and/or halogen and preferably aryl mono- to tri-substituted by $C_1$-$C_4$ alkyl, $C_1$-$C_4$ alkoxy, and/or halogen, such as 2-alkylphenyl, 3-alkylphenyl, 4-alkylphenyl, 2,3-dialkylphenyl, 2,4-dialkylphenyl, 2,5-dialkylphenyl, 2,4,6-trialkylphenyl, 2-alkoxyphenyl, 3-alkoxyphenyl, 4-alkoxyphenyl, 2,4-dialkoxyphenyl, and 4-chlorophenyl and more preferably methyl, ethyl, methoxy, ethoxy, fluorine and/or chlorine, mono- to tri-substituted phenyl, such as 2-methylphenyl, 3-methylphenyl, 4-methylphenyl, 4-methoxyphenyl, and 4-chlorophenyl,
- $C_7$-$C_{20}$ aralkyl mono- to penta-substituted by $C_1$-$C_8$ alkyl, $C_1$-$C_8$ alkoxy, and/or halogen and preferably aralkyl mono- to tri-substituted by $C_1$-$C_4$ alkyl, $C_1$-$C_4$ alkoxy, and/or halogen, such as 4-alkylphenylalkyl, 4-alkoxyphenylalkyl, 4-chlorophenylalkyl, and 3,5-dialkylphenylalkyl and more preferably methyl, ethyl, methoxy, ethoxy, fluorine and/or chlorine, mono- to tri-substituted phenylalkyl, such as 4-methylphenylmethyl, 4-methoxyphenylmethyl, and 4-chlorophenylmethyl,
- $C_3$-$C_{20}$ cycloalkyl mono- to penta-substituted by $C_1$-$C_8$ alkyl, $C_1$-$C_8$ alkoxy, and/or halogen and preferably $C_5$-$C_8$ cycloalkyl mono- to tri-substituted by $C_1$-$C_4$ alkyl, $C_1$-$C_4$ alkoxy, and/or halogen, such as 2-alkylcyclohexyl, 4-alkylcyclohexyl, 2-alkoxycyclohexyl, and 4-alkoxycyclohexyl and more preferably methyl, ethyl, methoxy, ethoxy, fluorine and/or chlorine, mono- to tri-substituted $C_5$-$C_8$ cycloalkyl, such as 2-methylcyclohexyl, 4-methylcyclohexyl, and 2-methoxycyclohexyl,
- $C_4$-$C_{20}$ cycloalkylalkyl mono- to penta-substituted by $C_1$-$C_8$ alkyl, $C_1$-$C_8$ alkoxy, and/or halogen and preferably $C_6$-$C_{12}$ cycloalkylalkyl mono-to tri-substituted by $C_1$-$C_4$ alkyl, $C_1$-$C_4$ alkoxy, and/or halogen, such as 2-alkylcyclohexylmethyl, 4-alkylcyclohexylmethyl, 2-alkoxycyclohexylmethyl, 4-alkoxycyclohexylmethyl, 2-halocyclohexylmethyl, and 4-halocyclohexylmethyl and more preferably methyl, ethyl, methoxy, ethoxy, fluorine and/or chlorine, mono- to tri-substituted $C_6$-$C_{12}$ cycloalkylalkyl such as 2-methoxycyclohexylmethyl, 2-methylcyclohexylmethyl, and 2-chlorocyclohexylmethyl, $R^1$ and $R^2$ individually denote

- $C_3$-$C_{20}$ alkoxycarbonylalkyl and preferably $C_3$-$C_{12}$ alkoxycarbonylalkyl and more preferably $C_3$-$C_8$ alkoxycarbonylalkyl such as methoxycarbonylmethyl, methoxycarbonylethyl, methoxycarbonylpropyl, methoxycarbonylbutyl and methoxycarbonylpentyl,
- $C_5$-$C_{30}$ acetalalkenyl and preferably $C_3$-$C_{12}$ acetalalkenyl such as 3,3-dimethoxy-1-propen-1-yl, 3,3- dimethoxy-2-methyl-1-propen-1-yl, and 3,3-dimethoxy-1-methyl-1-propen-1-yl, $C_7$–$C_{20}$ aralkenyl optionally mono- to penta-substituted by $C_1$–$C_8$ alkyl, $C_1$–$C_8$ alkoxy, and/or halogen and preferably $C_7$–$C_{12}$ aralkenyl mono- to tri-substituted by $C_1$–$C_4$ alkyl, $C_1$–$C_4$ alkoxy, and/or halogen, such as 2-phenethenyl, 2-(4-methylphenyl)ethenyl, 2-(4-chlorophenyl)ethenyl and 3-phenyl-2-propen-1-yl and more preferably methyl, ethyl, methoxy, ethoxy, fluorine and/or chlorine, and mono- to tri-substituted $C_8$–$C_{12}$-phenylalkenyl, hetaryl, e.g., five-membered cyclic hetero aromatics containing an oxygen or sulfur atom such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, and 1,3,4-triazol-2-yl, or together denote a $C_2$–$C_8$ alkylene chain such as —($CH_2$)—, —($CH_2$)$_2$—, —($CH_2$)$_3$—, —($CH_2$)$_4$—, —($CH_2$)$_5$—, —($CH_2$)$_6$—, —($CH_2$)$_7$—, —($CH_2$)$_8$—, preferably —($CH_2$)$_3$—, —($CH_2$)$_4$—, —($CH_2$)$_5$ and —($CH_2$)$_6$— and more preferably —($CH_2$)$_4$— and —($CH_2$)$_5$—, whilst one of the substituents $R^1$ and $R^2$ denotes hydrogen, and $R^3$ denotes hydrogen.

The β-hydroxycarboxylates I are suitable intermediates for the preparation of plant-protectants and pharmaceutically active substances (*Synthesis*, 571 to 590 (1989)).

EXAMPLES

General Reaction Equation

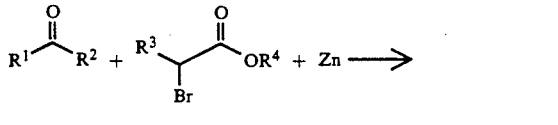

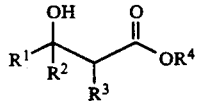

General Operating Instructions

In a three-necked flask having a capacity of 1 L and equipped with a reflux condenser, dropping funnel, internal thermometer, and stirrer there are placed 42.5 g (0.65 mol) of zinc powder and from 200 to 300 mg of iodine in 125 mL of methylene chloride and the mixture is subjected to vigorous stirring. Heating is continued until the methylene chloride boils under reflux and a mixture of 400 mmol of α-bromocarboxylates and 375 mmol of aldehyde or ketone is added dropwise. As soon as the iodine-tinted solution loses color the heat source is removed and the dropping rate is regulated in such a manner that the reaction solution continues to boil gently. On completion of the dropwise addition refluxing is continued for a period of 1 h. To the mixture there are added 250 mL of methyl-tert-butyl ether and hydrolysis is effected at from 0° to 10° C. using 250 mL of 2N sulfuric acid, (2N citric acid in the case of acid-sensitive substrates). The organic phase is separated, dried over sodium sulfate and concentrated. Vacuum distillation yields the pure Reformatskii products, as shown in the table below. Solid carbonyl compounds are dissolved in a little methylene chloride.

TABLE

| Example No. | $R^1$ | $R^2$ | $R^3$ | $R^4$ | Yield |
|---|---|---|---|---|---|
| 1 | Et— | H | H | Et | 88% |
| 2 | Bu— | H | H | Et | 87% |
| 3 | Iso—Pr— | H | H | Et | 88% |
| 4 | Ph— | H | H | Et | 95% |
| 5 | 4-ClPh— | H | H | Et | 95% |
| 6 | 4-MeOPh— | H | H | Et | 94% |
| 7 | 4-MeOPh— | H | Me | Et | 83% |
| 8 | Me—CH=CH— | H | H | Et | 91% |
| 9 | Ph—CH=CH— | H | H | Et | 92% |
| 10 | Furyl— | H | H | Et | 95% |
| 11 | Et— | Me | H | Et | 89% |
| 12 | Nonyl— | Et | H | Et | 92% |
| 13 | —($CH_2$)$_5$— | — | H | Me | 70% |
| 14 | Ph— | Me | H | Et | 75% |
| 15 | Ph— | Ph | H | Et | 80% |
| 16 | MeOOC—($CH_2$)$_4$— | H | H | Me | 91% |
| 17 | *(RO)$_2$CH—C(CH$_3$)=CH— | H | H | Me | 69% |
| 18 | *(RO)$_2$CH—CH=C(CH$_3$)— | H | H | Me | 84% |

*(RO)$_2$ = —O—CH$_2$—C(CH$_3$)$_2$—CH$_2$—O—: neopentylglycol acetal

Examples 19 to 22 were carried out following the general instructions given above, with the exception that the α-bromocarboxylate was first added dropwise followed by the electrophilic substance.

| | $R^2$ = H, $R^3$ = H, $R^4$ = Me | |
|---|---|---|
| Example No. | $R^1$ | Yield |
| 19 | 2-thienyl | 65% |
| 20 | 3-thienyl | 70% |
| 21 | (CH$_3$)$_2$C=CH—CH$_2$—CH$_2$—C(CH$_3$)=CH— | 80% |
| 22 | OHC—C(CH$_3$)=CH—CH=CH—CH=C(CH$_3$)— | 83%** |

**Product: CH$_3$OCO—CH$_2$—CH(OH)—C(CH$_3$)=CH—CH=CH—CH=C(CH$_3$)—CH(OH)—CH$_2$—COOCH$_3$ using 2 equivalents of BrCH$_2$—COOCH$_3$

We claim:

1. A process for the preparation of β-hydroxycarboxylates of the general formula I

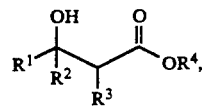

in which $R^1$ and $R^2$ and individually denote $C_1$–$C_{20}$ alkyl optionally substituted by $C_1$–$C_8$ alkoxy and/or halogen, $C_3$–$C_{20}$ alkoxycarbonylalkyl, $C_2$–$C_{20}$ alkenyl, $C_5$–$C_{30}$ acetalalkenyl, aryl optionally mono- to penta-substituted by $C_1$–$C_8$ alkyl, $C_1$–$C_8$ alkoxy, and/or halogen, $C_7$–$C_{20}$ aralkyl, $C_7$–$C_{20}$ aralkenyl, hetaryl, $C_3$–$C_{20}$ cycloalkyl, or $C_4$–$C_{20}$ cycloalkylalkyl, or together denote a $C_2$–$C_8$ alkylene chain and one or other of $R^1$ and $R^2$ denotes hydrogen, and $R^3$ denotes hydrogen, $C_1$–$C_{20}$ alkyl, $C_2$–$C_{20}$ alkenyl, aryl optionally mono- to penta-substituted by $C_1$–$C_8$ alkyl, $C_1$–$C_8$ alkoxy, and/or halogen, $C_7$–$C_{20}$ aralkyl, $C_3$–$C_{20}$ cycloalkyl, or $C_4$–$C_{20}$ cycloalkylalkyl, and $R^4$ denotes $C_1$–$C_{20}$ alkyl, $C_4$–$C_{20}$ alkenyl, $C_7$–$C_{20}$ aralkyl, $C_3$–$C_{20}$ cycloalkyl, or $C_4$–$C_{20}$ cycloalkylalkyl,

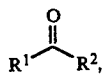 (II)

with α-bromocarboxylates of the general formula III

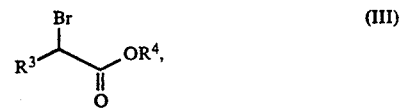

in which $R^3$ and $R^4$ have the meanings stated above, and with zinc in the presence of methylene chloride at a temperature ranging from 0° to 50° C.

* * * * *